US009060540B2

(12) United States Patent
Rochat et al.

(10) Patent No.: US 9,060,540 B2
(45) Date of Patent: Jun. 23, 2015

(54) PROBIOTICS TO INCREASE IGA SECRETION IN INFANTS BORN BY CAESAREAN SECTION

(75) Inventors: Florence Rochat, Montreux (CH); Marie-Claire Fichot, Blonay (CH)

(73) Assignee: Nestec S.A., Vevey (CH)

( * ) Notice: Subject to any disclaimer, the term of this patent is extended or adjusted under 35 U.S.C. 154(b) by 660 days.

(21) Appl. No.: 13/055,067

(22) PCT Filed: Jul. 15, 2009

(86) PCT No.: PCT/EP2009/059072
§ 371 (c)(1),
(2), (4) Date: Jan. 20, 2011

(87) PCT Pub. No.: WO2010/010021
PCT Pub. Date: Jan. 28, 2010

(65) Prior Publication Data
US 2011/0129452 A1 Jun. 2, 2011

(51) Int. Cl.
*A01N 63/00* (2006.01)
*A23L 1/30* (2006.01)
*A23L 1/29* (2006.01)

(52) U.S. Cl.
CPC . *A23L 1/30* (2013.01); *A23L 1/296* (2013.01); *A23L 1/3014* (2013.01); *A23V 2002/00* (2013.01); *A61K 35/745* (2013.01); *A61K 35/747* (2013.01)

(58) Field of Classification Search
None
See application file for complete search history.

(56) References Cited

U.S. PATENT DOCUMENTS

2006/0067921 A1* 3/2006 Conway .................... 424/93.45

FOREIGN PATENT DOCUMENTS

| CA | 2678994 | 3/2008 |
|----|---------|--------|
| EP | 0577903 | 1/1994 |
| EP | 0768375 | 4/1997 |
| EP | 1776877 | 4/2007 |
| EP | 1974743 | 10/2008 |
| WO | 9700078 | 1/1997 |
| WO | 0053200 | 9/2000 |
| WO | WO 2006/108824 | * 10/2006 |
| WO | 2007101675 | 9/2007 |

OTHER PUBLICATIONS

Chouraqui et al. "Assessment of the safety, tolerance, and protective effect against diarrhea of infant formulas containing mixtures of probiotics or probiotics and prebiotics in a randomized controlled trial". American Journal of Clinical Nutrition, (May 2008), vol. 87, No. 5, pp. 1365-1373.*

Bakker-Zierikzee et al., Effects of infant formula containing a mixture of galacto- and fructo-oligosaccharides or viable Bifidobacterium animalis on the intestinal microflora during the first 4 months of life, British Journal of Nutrition (2005), vol. 94, pp. 783-790.

Inoue et al., "Oral treatment with probiotic *Lactobacillus johnsonii* NCC533 (La1) for a specific part of the weaning period prevents the development of atopic dermatitis induced after maturation in model mice, NC/Nga," British Journal of Dermatology, vol. 156, No. 3 (2007), pp. 499-509—XP-002521659.

Rastall et al., "Modulation of the microbial ecology of the human colon by probiotics, prebiotics and synbiotics to enhance human health: An overview of enabling science and potential applications," FEMS Microbiology Ecology, vol. 52, No. 2 (2005), pp. 145-152—XP-25292521.

Chen et al., "Development of intestinal bifidobacteria and lactobacilli in breast-fed neonates," Clinical Nutrition, vol. 26, No. 5 (2007), pp. 559-566—XP-2521660.

Huurre et al., "Mode of Delivery—Effects on Gut Microbiota and Humoral Immunity," Neonatology, vol. 93, No. 4 (2008), pp. 236-240—XP-8104058.

Heinrich et al., "Mode of delivery and development of atopic disease during the first 2 years of life," Pediatr Allergy Immunol, vol. 15 (2004) pp. 48-54—XP002435767.

Agostoni et al., "Probiotic Bacteria in Dietetic Products for Infants: A Commentary by the ESPGHAN Committee on Nutrition," Journal of Pediatric Gastroenterology and Nutrition, vol. 38, No. 4 Apr. 2004, pp. 365-374—XP 009069353.

Bakker-Zierikzee et al., "Faecal SIgA secretion in infants fed on pre- or probiotic infant formula," Pediatric Allergy and Immunology, vol. 17, No. 2 (2006), pp. 134-140—XP-002521656.

Martino et al., "Relationship between early intestinal colonization, mucosal immunoglobulin A production and systemic immune development," Clinical and Experimental Allergy, vol. 38, No. 1 Jan. 2008, pp. 69-78—XP-002521657.

Vancikova et al., "The Early Postnatal Development of Salivary Antibody and Immunoglobulin Response in Children Orally Colonized with a Nonpathogenic, Probiotic Strain of *E. coli*," vol. 48, No. 2 Jan. 1, 2003, pp. 281-287—XP-008104010.

Fukushima et al., "Effect of a probiotic formula on intestinal immunoglobulin A production in healthy children," vol. 42, No. 1-2 Jun. 30, 1998, pp. 365-374—XP002521672.

Cano et al., "Adjuvant effects of *Lactobacillus casei* added to a renutrition diet in a malnourished mouse model", Biocell 2002, 26(1) p. 35-48.

Diaz-Ropero et al., "Two *Lactobacillus* strains, isolated from brest mil, differently modulate the immune response", Journal of Applied Microbiology ISSN 1364-5072 p. 337-343.

(Continued)

*Primary Examiner* — Vera Afremova
(74) *Attorney, Agent, or Firm* — K&L Gates LLP

(57) ABSTRACT

Use of probiotic bacteria in the manufacture of a medicament or therapeutic nutritional composition for increasing IgA secretion in an infant delivered by cesarean section during the first four months of the life of the infant.

18 Claims, No Drawings

(56) References Cited

OTHER PUBLICATIONS

Gibson et al., "Dietary Modulation of the Human Colonic Microbiota: Introducing the Concept of Prebiotics", American Institute of Nutrition, 1995 p. 1401-1412.

Grolund et al., "Fecal Microflora in Healthy Infants Born by Different Methods of Delivery: Permanent Changes in Intestinal Flora After Cesarean Delivery", Journal of Pediatric Gastroenterology & Nutrition: Jan. 1999—vol. 28, Issue 1 p. 19-25.

Salminen et al., "Probiotics: how should they be defined?", Trends in Food Science & Technology 10 (1999) p. 107-110.

* cited by examiner

PROBIOTICS TO INCREASE IGA SECRETION IN INFANTS BORN BY CAESAREAN SECTION

FIELD OF THE INVENTION

This invention relates to the administration of probiotic bacteria to infants delivered by Cesarean section to increase IgA secretion during the first four to six months of life.

BACKGROUND TO THE INVENTION

Immediately before birth, the gastro-intestinal tract of a baby is thought to be sterile. During the normal process of birth, it encounters bacteria from the digestive tract, skin and environment of the mother and starts to become colonised. The faecal microbiota of a healthy, vaginally-delivered, breast-fed infant of age 2 to 4 weeks which may be taken as the optimum microbiota for this age group is dominated by Bifidobacteria species with some *Lactobacillus* species and lesser amounts of *Bacteroides* such as *Bacteriodes fragilis* species, at the expense of potential pathogens such as Clostridia. After the completion of weaning at about 2 years of age, a pattern of gut microbiota that resembles the adult pattern becomes established.

It should be noted that, in the healthy, vaginally-delivered, breast-fed infant, Bifidobacteria form the basis of the microbiota accounting for 60-90% of total bacteria in the infant gut. Breast feeding also promotes intestinal barrier development which, together with bifidobacterial domination leads to enhanced absorption and therefore utilisation of ingested nutrition.

Grönlund et al have studied the faecal microbiota of healthy infants born by cesarean section and compared it with that of a comparable group of infants born by vaginal delivery. They concluded that the gut flora of infants born by cesarean delivery may be disturbed for up to six months after the birth. Specifically they noted that the rates of colonisation by Bifidobacteria and Lactobacilli in the cesarean group reached the rates of colonisation in the vaginally delivered group only after one month and ten days respectively (Grönlund et al, "Fecal Microflora in Healthy Infants Born by Different Methods of Delivery: Permanent Changes in Intestinal Flora After Cesarean Delivery", Journal of Pediatric Gastroenterology and Nutrition, 28:19-25).

Other workers have suggested that this delayed/aberrant colonisation may have specific consequences in terms of the subsequent development of the infant and have investigated a possible link between these consequences and differences in the gut microbiota. For example, Martino et al investigated colonisation patterns and mucosal IgA production at 6 months of age in relation to early exposures, systemic immune development and early allergic outcomes in a cohort who had received either the probiotic *Lactobacillus acidophilus* strain LAVRI-A1 or a placebo (Martino et al, "Relationship between early intestinal colonisation, mucosal immunoglobulin A production and systemic immune development" Clinical and Experimental Allergy, 38, 69-78).

Mother's milk is recommended for all infants. However, in some cases breast feeding is inadequate or unsuccessful for medical reasons or the mother chooses not to breast feed. Infant formulae have been developed for these situations.

In the recent past, certain strains of bacteria have attracted considerable attention because they have been found to exhibit valuable properties for man if ingested. In particular, specific strains of the genera Lactobacilli and Bifidobacteria have been found to be able to colonise the intestine, to reduce the capability of pathogenic bacteria to adhere to the intestinal epithelium, to have immunomodulatory effects and to assist in the maintenance of well-being. Such bacteria are sometimes called probiotics and it has already been proposed to add suitable probiotic bacteria to infant formulas.

Extensive studies have been carried out to identify new probiotic strains. For example, EP 0 199 535, EP 0 768 375, WO 97/00078, EP 0 577 903 and WO 00/53200 disclose specific strains of Lactobacilli and Bifidobacteria and their beneficial effects.

For example, Vancikova et al reported that early artificial mucosal colonisation with the probiotic bacterial strain *E. coli* O83 stimulates the mucosal immune system to produce non-specific secretory IgA in addition to specific antibodies (Vancikova et al, "The early postnatal development of salivary antibody and immunoglobulin response in children orally colonised with a non-pathogenic, probiotic strain of *E. coli*" Folia Microbiol (Praha) 2003; 48:281-7).

Fukushima et al studied the effect of a probiotic *Bifidobacterium lactis* strain on IgA secretion in a cohort of older children (15 to 31 months old) and found increased levels of total IgA and anti-polio virus IgA.

The proportion of cesarean deliveries continues to increase reaching as much as 70% of all births in some countries. It is therefore clear that there is a need to provide a means to reduce the risk that infants born by cesarean section do not suffer adverse health consequences as a result of their mode of delivery. This need is particularly acute given the current practice of routinely administering prophylactic doses of antibiotics to pregnant women who undergo an elective cesarean delivery.

SUMMARY OF THE INVENTION

Accordingly the present invention provides the use of probiotic bacteria in the manufacture of a medicament or therapeutic nutritional composition for increasing IgA secretion in an infant delivered by cesarean section during the first four months of the life of the infant.

The invention extends to the use of probiotic bacteria in the manufacture of a medicament or therapeutic nutritional composition for improving the mucosal immune defences of an infant delivered by cesarean section during the first four months of the life of the infant.

The invention further extends to a method of increasing IgA secretion in an infant delivered by cesarean section during the first four months of the life of the infant comprising providing a therapeutic amount of probiotic bacteria to an infant born by cesarean section and in need of the same.

In a further aspect the invention provides a method of improving the mucosal immune defences in an infant delivered by cesarean section during the first four months of the life of the infant comprising providing a therapeutic amount of probiotic bacteria to an infant born by cesarean section and in need of the same. Without wishing to be bound by theory, the present inventors believe that administration of probiotic bacteria to an infant delivered by cesarean section in some way as yet incompletely understood primes the gastrointestinal tract of the infant to favour subsequent colonisation by those species of Bifidobacteria which are commonly found in the tracts of healthy, vaginally-delivered, breast-fed infants and that the beneficial colonisation increases total IgA secretion (i.e. secretion of both specific and non-specific IgA) to levels comparable to those found naturally in this reference population. One effect of increased IgA secretion is to enhance the mucosal immune defences of the infant.

It should be noted that it is neither the object nor the effect of such treatment to promote colonisation by the species of probiotic that is administered but rather to promote colonisation with other species so as to achieve an early bifidogenic intestinal microbiota comparable with that found in healthy, breast-fed, vaginally-delivered infants.

DETAILED DESCRIPTION OF THE INVENTION

In this specification, the following terms have the following meanings:—

"infant" means a child under the age of 12 months.

"prebiotic" means a non-digestible food ingredient that beneficially affects the host by selectively stimulating the growth and/or activity of one or a limited number of bacteria in the colon and thus improves host health (Gibson and Roberfroid "Dietary Modulation of the Human Colonic Microbiota: Introducing the Concept of Prebiotics" J. Nutr 125: 1401-1412).

"probiotic" means microbial cell preparations or components of microbial cells with a beneficial effect on the health or well-being of the host. (Salminen S, Ouwehand A. Benno Y. et al "Probiotics: how should they be defined" Trends Food Sci. Technol. 1999:10 107-10).

All references to percentages are percentages by weight unless otherwise stated. The probiotic bacteria may be any lactic acid bacteria or Bifidobacteria with established probiotic characteristics which are also capable of promoting the development of an early bifidogenic intestinal microbiota. Suitable probiotic lactic acid bacteria include *Lactobacillus rhamnosus* ATCC 53103 obtainable inter alia from Valio Oy of Finland under the trade mark LGG, *Lactobacillus rhamnosus* CGMCC 1.3724, *Lactobacillus reuteri* ATCC 55730 and *Lactobacillus reuteri* DSM 17938 obtainable from Biogaia, *Lactobacillus fermentum* VR1003 and *Lactobacillus paracasei* CNCM I-2116.

Suitable probiotic Bifidobacteria strains include *Bifidobacterium longum* ATCC BAA-999 sold by Morinaga Milk Industry Co. Ltd. of Japan under the trade mark BB536, the strain of *Bifidobacterium breve* sold by Danisco under the trade mark Bb-03, the strain of *Bifidobacterium breve* sold by Morinaga under the trade mark M-16V and the strain of *Bifidobacterium breve* sold by Institut Rosell (Lallemand) under the trade mark R0070. A particularly preferred *Bifidobacterium* strain is *Bifidobacterium lactis* CNCM I-3446 which may be obtained from the Christian Hansen company of Denmark under the trade mark Bb12. A mixture of suitable probiotic lactic acid bacteria and Bifidobacteria may be used.

A suitable daily dose of the probiotic bacteria is from 10e3 to 10 µl colony forming units (cfu), more preferably from 10e7 to 10e 10 cfu.

Preferably the probiotic bacteria are co-administered with a prebiotic. Suitable prebiotics include certain oligosaccharides, such as fructooligosaccharides (FOS) and galactooligosaccharides (GOS). A combination of prebiotics may be used such as 90% GOS with 10% short chain fructo-oligosaccharides such as the product sold under the trade mark Beneo® P95 or 10% inulin such as the product sold under the trade mark Beneo® HP, ST or HSI.

A particularly preferred prebiotic is a mixture of galacto-oligosaccharide(s), N-acetylated oligosaccharide(s) and sialylated oligosaccharide(s) in which the N-acetylated oligosaccharide(s) comprise 0.5 to 4.0% of the oligosaccharide mixture, the galacto-oligosaccharide(s) comprise 92.0 to 98.5% of the oligosaccharide mixture and the sialylated oligosaccharide(s) comprise 1.0 to 4.0% of the oligosaccharide mixture. This mixture is hereinafter referred to as "the preferred prebiotic mixture".

Suitable N-acetylated oligosaccharides include GalNAcα1,3Galβ1,4Glc and Galβ1,6GalNAcα1,3Galβ1,4Glc. The N-acetylated oligosaccharides may be prepared by the action of glucosaminidase and/or galactosaminidase on N-acetyl-glucose and/or N-acetyl galactose. Equally, N-acetyl-galactosyl transferases and/or N-acetyl-glycosyl transferases may be used for this purpose. The N-acetylated oligosaccharides may also be produced by fermentation technology using respective enzymes (recombinant or natural) and/or microbial fermentation. In the latter case the microbes may either express their natural enzymes and substrates or may be engineered to produce respective substrates and enzymes. Single microbial cultures or mixed cultures may be used. N-acetylated oligosaccharide formation can be initiated by acceptor substrates starting from any degree of polymerisation (DP) from DP=1 onwards. Another option is the chemical conversion of keto-hexoses (e.g. fructose) either free or bound to an oligosaccharide (e.g. lactulose) into N-acetylhexosamine or an N-acetylhexosamine containing oligosaccharide as described in Wrodnigg, T. M.; Stutz, A. E. (1999) Angew. Chem. Int. Ed. 38:827-828.

Suitable galacto-oligosaccharides include Galβ1,6Gal, Galβ1,6Galβ1,4Glc Galβ1,6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc Galβ1,3Galβ1,6Galβ1,4Glc, Galβ1,3Galβ1,3Galβ1,4Glc, Galβ1,4Galβ1,4Glc and Galβ1,4Galβ1,4Galβ1,4Glc. Synthesised galacto-oligosaccharides such as Galβ1,6Galβ1,4Glc Galβ1,6Galβ1,6Glc, Galβ1,3Galβ1,4Glc, Galβ1,6Galβ1,6Galβ1,4Glc, Galβ1,6Galβ1,3Galβ1,4Glc and Galβ1,3Galβ1,6Galβ1,4Glc, Galβ1,4Galβ1,4Glc and Galβ1,4Galβ1,4Galβ1,4Glc and mixtures thereof are commercially available under the trade marks Vivinal® and Elix'or®. Other suppliers of oligosaccharides are Dextra Laboratories, Sigma-Aldrich Chemie GmbH and Kyowa Hakko Kogyo Co., Ltd. Alternatively, specific glycoslytransferases, such as galactosyltransferases may be used to produce neutral oligosaccharides.

Suitable sialylated oligosaccharides include NeuAcα2,3Galβ1,4Glc and NeuAcα2,6Galβ1,4Glc. These sialylated oligosaccharides may be isolated by chromatographic or filtration technology from a natural source such as animal milks. Alternatively, they may also be produced by biotechnology using specific sialyltransferases either by enzyme based fermentation technology (recombinant or natural enzymes) or by microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP) from DP=1 onwards.

The probiotic bacteria are preferably administered to the infant immediately after delivery and thereafter for at least the first two to four months of the life of the infant.

The probiotic bacteria may be administered directly to the infant or, if the mother is breast-feeding, via the mother. If the probiotic bacteria are to be administered via the mother, they may be supplied to the mother as a supplement in the form of tablets, capsules, pastilles, chewing gum or a liquid for example. The supplement preferably also contains the oligosaccharide mixture described above in an amount of from in an amount of from 0.2 to 10 g/day. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. The supplement may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. In all cases, such further components will be selected having regard to their suitability for the intended recipient.

Alternatively, the probiotic bacteria may be administered to the mother in the form of a therapeutic nutritional composition. The composition may be a nutritionally complete formula.

A nutritionally complete formula for administration to lactating women according to the invention may comprise a source of protein. Any suitable dietary protein may be used for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred. The composition may also contain a source of carbohydrates and a source of fat.

If the formula includes a fat source in addition to the DHA, the fat source preferably provides 5% to 40% of the energy of the formula; for example 20% to 30% of the energy. A suitable fat profile may be obtained using a blend of canola oil, corn oil and high-oleic acid sunflower oil.

A source of carbohydrate may be added to the formula. It preferably provides 40% to 80% of the energy of the formula. Any suitable carbohydrate may be used, for example sucrose, lactose, glucose, fructose, corn syrup solids, maltodextrins, and mixtures thereof. Dietary fibre may also be added if desired. Dietary fibre passes through the small intestine undigested by enzymes and functions as a natural bulking agent and laxative. Dietary fibre may be soluble or insoluble and in general a blend of the two types is preferred. Suitable sources of dietary fibre include soy, pea, oat, pectin, guar gum, gum Arabic. Preferably, if fibre is present, the fibre content is between 2 and 40 g/l of the formula as consumed, more preferably between 4 and 10 g/l. In addition, the formula also preferably contains the preferred prebiotic mixture in an amount of from 2.5 to 15.0% by weight on a dry matter basis, preferably from 3.0 to 12.0%, more preferably from 4.0 to 7.0%.

The formula may also contain minerals and micronutrients such as trace elements and vitamins in accordance with the recommendations of Government bodies such as the USRDA. For example, the formula may contain per daily dose one or more of the following micronutrients in the ranges given:—300 to 500 mg calcium, 50 to 100 mg magnesium, 150 to 250 mg phosphorus, 5 to 20 mg iron, 1 to 7 mg zinc, 0.1 to 0.3 mg copper, 50 to 200 µg iodine, 5 to 15 µg selenium, 1000 to 3000 µg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 µg Vitamin B12, 100 to 800 µg folic acid, 30 to 70 µg biotin, 1 to 5 µg Vitamin D, 3 to 10 IU Vitamin E.

One or more food grade emulsifiers may be incorporated into the formula if desired; for example diacetyl tartaric acid esters of mono- and di-glycerides, lecithin and mono- and di-glycerides. Similarly suitable salts and stabilisers may be included.

The formula is preferably enterally administrable; for example in the form of a powder for re-constitution with milk or water. Alternatively, or in the case of infants who are not breast fed, the probiotic may be administered as a supplement, for example as a daily dose of 10e10 cfu dissolved in water and administered on a spoon.

For infants who are not breast fed, the probiotic bacteria may alternatively conveniently be administered in an infant formula.

An infant formula for use according to the present invention may contain a protein source in an amount of not more than 2.0 g/100 kcal, preferably 1.8 to 2.0 g/100 kcal. The type of protein is not believed to be critical to the present invention provided that the minimum requirements for essential amino acid content are met and satisfactory growth is ensured although it is preferred that over 50% by weight of the protein source is whey. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in whatever proportions are desired.

The proteins may be intact or hydrolysed or a mixture of intact and hydrolysed proteins. It may be desirable to supply partially hydrolysed proteins (degree of hydrolysis between 2 and 20%), for example for infants believed to be at risk of developing cows' milk allergy. If hydrolysed proteins are required, the hydrolysis process may be carried out as desired and as is known in the art. For example, a whey protein hydrolysate may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

The infant formula may contain a carbohydrate source. Any carbohydrate source conventionally found in infant formulae such as lactose, saccharose, maltodextrin, starch and mixtures thereof may be used although the preferred source of carbohydrates is lactose. Preferably the carbohydrate sources contribute between 35 and 65% of the total energy of the formula.

The infant formula may contain a source of lipids. The lipid source may be any lipid or fat which is suitable for use in infant formulas. Preferred fat sources include palm olein, high oleic sunflower oil and high oleic safflower oil. The essential fatty acids linoleic and α-linolenic acid may also be added as may small amounts of oils containing high quantities of preformed arachidonic acid and docosahexaenoic acid such as fish oils or microbial oils. In total, the fat content is preferably such as to contribute between 30 to 55% of the total energy of the formula. The fat source preferably has a ratio of n-6 to n-3 fatty acids of about 5:1 to about 15:1; for example about 8:1 to about 10:1.

The infant formula may also contain all vitamins and minerals understood to be essential in the daily diet and in nutritionally significant amounts. Minimum requirements have been established for certain vitamins and minerals. Examples of minerals, vitamins and other nutrients optionally present in the infant formula include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population.

If necessary, the infant formula may contain emulsifiers and stabilisers such as soy lecithin, citric acid esters of mono- and di-glycerides, and the like.

In addition, the infant formula also preferably contains the preferred prebiotic mixture in an amount of from 2.5 to 15.0% by weight on a dry matter basis, preferably from 3.0 to 12.0%, more preferably from 4.0 to 7.0%.

The infant formula may optionally contain other substances which may have a beneficial effect such as lactoferrin, nucleotides, nucleosides, and the like.

Both the infant formula and the nutritional formula described above may be prepared in any suitable manner. For example, they may be prepared by blending together the protein, the carbohydrate source, and the fat source in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture is then homogenised; for example in two stages.

The liquid mixture may then be thermally treated to reduce bacterial loads, by rapidly heating the liquid mixture to a temperature in the range of about 80° C. to about 150° C. for about 5 seconds to about 5 minutes, for example. This may be carried out by steam injection, autoclave or by heat exchanger; for example a plate heat exchanger.

Then, the liquid mixture may be cooled to about 60° C. to about 85° C.; for example by flash cooling. The liquid mixture may then be again homogenised; for example in two stages at about 10 MPa to about 30 MPa in the first stage and about 2 MPa to about 10 MPa in the second stage. The homogenised mixture may then be further cooled to add any heat sensitive components; such as vitamins and minerals. The pH and solids content of the homogenised mixture are conveniently adjusted at this point.

The homogenised mixture is transferred to a suitable drying apparatus such as a spray drier or freeze drier and converted to powder. The powder should have a moisture content of less than about 5% by weight.

The selected probiotic bacteria may be cultured according to any suitable method and prepared for addition to the nutritional or infant formula by freeze-drying or spray-drying for example. Alternatively, bacterial preparations can be bought from specialist suppliers such as Christian Hansen and Valio already prepared in a suitable form for addition to food products such as nutritional and infant formulas. The probiotic bacteria may be added to the formula in an amount between 10e3 and 10e12 cfu/g powder, more preferably between 10e7 and 10e12 cfu/g powder.

The invention will now be further illustrated by reference to the following examples:—

Example 1

An example of the composition of a suitable infant formula to be used in the present invention is given below

| Nutrient | per 100 kcal | per litre |
| --- | --- | --- |
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |
| Bifidobacterium lactis CNCM I-3446 | $2.10^7$ cfu/g of powder, live bacteria | |

Example 2

Objective

A clinical trial was developed to assess the effect of a standard formula and Nan® containing or not a probiotic, Bifidobacterium longum (BL999, ATCC BAA-999; Morinaga, Japan), on immune development of infant born by C-section or by vaginal delivery.

Methods:

A randomized, double blind, controlled trial of 3 groups:

Group fed with a Standard formula (casein predominant, high in phosphates and protein, low in lactose);

Group fed with Nan® (Infant Formula, commercially available from Nestlé Switzerland, 30/70 Casein/Whey ratio, low proteins (1.8 g/100 Kcal); low phosphate (31 mg/100 Kcal) and high lactose levels (11.1 g/100 Kcal);

Group fed with Nan®+ BL999

A reference Breast Fed group was also analyzed.

Healthy singleton term infants born via C-section received the study formula for 4 months.

Stool IgA levels (μg/mL) were measure at 2 months using conventional methods.

Results:

Independently of the mode of feeding infant born via C-section have lower of fecal IgA. Interestingly, Nan® with a probiotic BL999 promote higher production of fecal IgA than a standard formula or a NAN without probiotic.

Mean absolute IgA (($\mu$g/mL) at two months:

| Mode of delivery | Standard formula | NAN | NAN + BL999 | Breast-fed |
|---|---|---|---|---|
| Vaginal delivery | 25.31 | 37.24 | 39.61 | 56.06 |
| C-section | 19.37 | 23.11 | 33.23 | 54.20 |

CONCLUSIONS

These data show that the infant born by C-section have a lower production of IgA and that infant formulae enriched with a probiotic as BL999 enhance immune functions of infant born via C-Section compared to standard formula. Their IgA values tend to be closer to the breast-fed.

The invention claimed is:

1. A method for increasing IgA secretion in an infant delivered by caesarean section during the first four months of the life of the infant comprising administering to the infant a composition comprising a probiotic bacteria, a protein source, and an oligosaccharide mixture, the composition is administered to the infant in a therapeutically-effective amount to promote colonization of microorganism species other than the probiotic bacteria that is administered, the composition comprises the probiotic bacteria in an amount between $10^7$ and $10^{12}$ cfu/g, the probiotic bacteria comprises a strain selected from the group consisting of *Lactobacillus rhamnosus* ATCC 53103, *Lactobacillus rhamnosus* CGMCC 1.3724, *Lactobacillus reuteri* ATCC 55730, *Lactobacillus reuteri* DSM 17938, *Lactobacillus fermentum* VRI 003 (NM02/31074), *Lactobacillus paracasei* CNCM I-2116, *Bifidobacterium lactis* CNCM I-3446, *Bifidobacterium longum* ATCC BAA-999, and *Bifidobacterium breve* Bb-03, the protein source comprising at least 50% whey by weight of the protein source, the protein source is present in the composition in an amount of not more than 2.0 g/100 kcal of the composition, and the oligosaccharide mixture comprising galacto-oligosaccharides, N-acetylated oligosaccharides and sialylated oligosaccharides in which the N-acetylated oligosaccharides are 0.5 to 4.0% of the oligosaccharide mixture, the galacto-oligosaccharides are 92.0 to 98.5% of the oligosaccharide mixture and the sialylated oligosaccharides are 1.0 to 4.0% of the oligosaccharide mixture by weight.

2. A method for improving the mucosal immune defenses of an infant delivered by caesarean section during the first four months of the life of the infant comprising administering to the infant a composition comprising a probiotic bacteria, a protein source, and an oligosaccharide mixture, the composition is administered to the infant in a therapeutically-effective amount to promote colonization of microorganism species other than the probiotic bacteria that is administered, the composition comprises the probiotic bacteria in an amount between $10^7$ and $10^{12}$ cfu/g, the probiotic bacteria comprises a strain selected from the group consisting of *Lactobacillus rhamnosus* ATCC 53103, *Lactobacillus rhamnosus* CGMCC 1.3724, *Lactobacillus reuteri* ATCC 55730, *Lactobacillus reuteri* DSM 17938, *Lactobacillus fermentum* VRI 003 (NM02/31074), *Lactobacillus paracasei* CNCM I-2116, *Bifidobacterium lactis* CNCM I-3446, *Bifidobacterium longum* ATCC BAA-999, and *Bifidobacterium breve* Bb-03, the protein source comprising at least 50% whey by weight of the protein source, the protein source is present in the composition in an amount of not more than 2.0 g/100 kcal of the composition, and the oligosaccharide mixture comprising galacto-oligosaccharides, N-acetylated oligosaccharides and sialylated oligosaccharides in which the N-acetylated oligosaccharides are 0.5 to 4.0% of the oligosaccharide mixture, the galacto-oligosaccharides are 92.0 to 98.5% of the oligosaccharide mixture and the sialylated oligosaccharides are 1.0 to 4.0% of the oligosaccharide mixture by weight.

3. The method of claim 1, wherein the probiotic bacteria is a strain selected from the group consisting of *Lactobacillus rhamnosus* ATCC 53103, *Lactobacillus rhamnosus* CGMCC 1.3724, *Lactobacillus reuteri* ATCC 55730, *Lactobacillus reuteri* DSM 17938, *Lactobacillus fermentum* VRI 003 (NM02/31074) and *Lactobacillus paracasei* CNCM I-2116.

4. The method of claim 1, wherein the probiotic is a strain selected from the group consisting of *Bifidobacterium lactis* CNCM I-3446, *Bifidobacterium longum* ATCC BAA-999, *Bifidobacterium breve* Bb-03.

5. The method of claim 1 wherein the protein source has a 30:70 casein:whey ratio.

6. The method of claim 1 wherein the composition is administered to the infant immediately after delivery and thereafter for at least 2 months.

7. The method of claim 1, wherein the composition is administered to the infant for at least 4 months after delivery.

8. The method of claim 1, wherein the composition is administered to the infant via a breast-feeding mother.

9. The method of claim 1, wherein the composition is an infant formula.

10. The method of claim 2, wherein the probiotic bacteria is a strain selected from the group consisting of *Lactobacillus rhamnosus* ATCC 53103, *Lactobacillus rhamnosus* CGMCC 1.3724, *Lactobacillus reuteri* ATCC 55730, *Lactobacillus reuteri* DSM 17938, *Lactobacillus fermentum* VRI 003 (NM02/31074) and *Lactobacillus paracasei* CNCM I-2116.

11. The method of claim 2, wherein the probiotic is a strain selected from the group consisting of *Bifidobacterium lactis* CNCM I-3446, *Bifidobacterium longum* ATCC BAA-999, *Bifidobacterium breve* Bb-03.

12. The method of claim 2 wherein the protein source is present in an amount from 1.8 to 2.0 g/l 00 kcal of the composition.

13. The method of claim 2 wherein the composition is administered to the infant immediately after delivery and thereafter for at least 2 months.

14. The method of claim 2, wherein the composition is administered to the infant for at least 4 months after delivery.

15. The method of claim 2, wherein the composition is administered to the infant via a breast-feeding mother.

16. The method of claim 2, wherein the composition is an infant formula.

17. The method of claim 1, wherein the protein source is present in an amount from 1.8 to 2.0 g/100 kcal of the composition.

18. A method comprising administering to an infant delivered by caesarean section during the first four months of the life of the infant a composition comprising a probiotic bacteria, a protein source, and an oligosaccharide mixture, the composition is administered to the infant in a therapeutically-effective amount to promote colonization of microorganism species other than the probiotic bacteria that is administered, the protein source comprising at least 50% whey by weight of the protein source, the protein source is present in the composition in an amount of 1.8 to 2.0 g/100 kcal of the composition, wherein the probiotic bacteria is *Bifidobacterium longum* ATCC BAA-999.

* * * * *